US 6,988,392 B2

(12) United States Patent
Barbé et al.

(10) Patent No.: US 6,988,392 B2
(45) Date of Patent: Jan. 24, 2006

(54) RELAXATION-TYPE VISCOSIMETER HAVING A MAGNETIC FIELD GENERATOR AND METHOD THEREFOR

(75) Inventors: Jean-Charles Barbé, Grenoble (FR); Michel Daniel, St Martin d'Uriage (FR); Jacky Bancillon, St Egréve (FR)

(73) Assignee: Commissariat a l'Energie Atomique, Paris (FR)

( * ) Notice: Subject to any disclaimer, the term of this patent is extended or adjusted under 35 U.S.C. 154(b) by 0 days.

(21) Appl. No.: 10/148,381

(22) PCT Filed: Dec. 14, 2000

(86) PCT No.: PCT/FR00/03522

§ 371 (c)(1),
(2), (4) Date: May 30, 2002

(87) PCT Pub. No.: WO01/44785

PCT Pub. Date: Jun. 21, 2001

(65) Prior Publication Data

US 2002/0178796 A1 Dec. 5, 2002

(30) Foreign Application Priority Data

Dec. 17, 1999 (FR) .................................. 99 16020

(51) Int. Cl.
*G01N 11/02* (2006.01)

(52) U.S. Cl. ..................................... 73/54.01; 73/54.02

(58) Field of Classification Search ............... 73/54.01, 73/54.02
See application file for complete search history.

(56) References Cited

U.S. PATENT DOCUMENTS

| 2,149,847 A | * | 3/1939 | Kolin ....................... 73/861.13 |
| H0093 H | * | 7/1986 | Matta et al. ................ 73/54.11 |
| 4,868,769 A | * | 9/1989 | Persson ........................ 702/30 |
| 5,040,410 A | | 8/1991 | Chu et al. |
| 5,177,997 A | * | 1/1993 | Maciejewski .............. 73/54.24 |
| 5,277,058 A | * | 1/1994 | Kalyon et al. ............. 73/54.11 |
| 5,629,209 A | * | 5/1997 | Braun et al. .................. 436/69 |
| 2001/0042400 A1 | * | 11/2001 | Boyle et al. ............... 73/54.28 |

FOREIGN PATENT DOCUMENTS

| DE | 197 45 807 A1 | | 5/1999 |
| FR | 2 756 924 | | 6/1998 |
| GB | 1160706 | * | 8/1969 |
| GB | 2 337 822 A | | 12/1999 |

OTHER PUBLICATIONS

B. Gauthier-Manuel, R. Meyer and P. Pieranski, "The Sphere Rheometer:I..Quasistatic Measurements", Jul. 1984, Journal of Physics E. Scientific Instruments, pp. 1177-1182.

* cited by examiner

Primary Examiner—Michael Cygan
(74) Attorney, Agent, or Firm—Pearne & Gordon LLP

(57) ABSTRACT

The process for measuring viscosity relies on the observation of the relaxation of a sample drop (A) initially flattened between two plates (7,8), normally without any contact with them due to a gas layer blown through their opposite faces (10, 11); one correlates the observed phenomenon with a relaxation model fitting each portion of the measurement curve so as to estimate concurrently the viscosity and the shear rate, then the sensitiveness of the viscosity to the shear rate by compiling the said portions. The proposed viscometer includes a variable magnetic field generator (16) to produce, using a removable screen (18), various stirring and shears in the sample (A).

4 Claims, 2 Drawing Sheets

Figure 1:
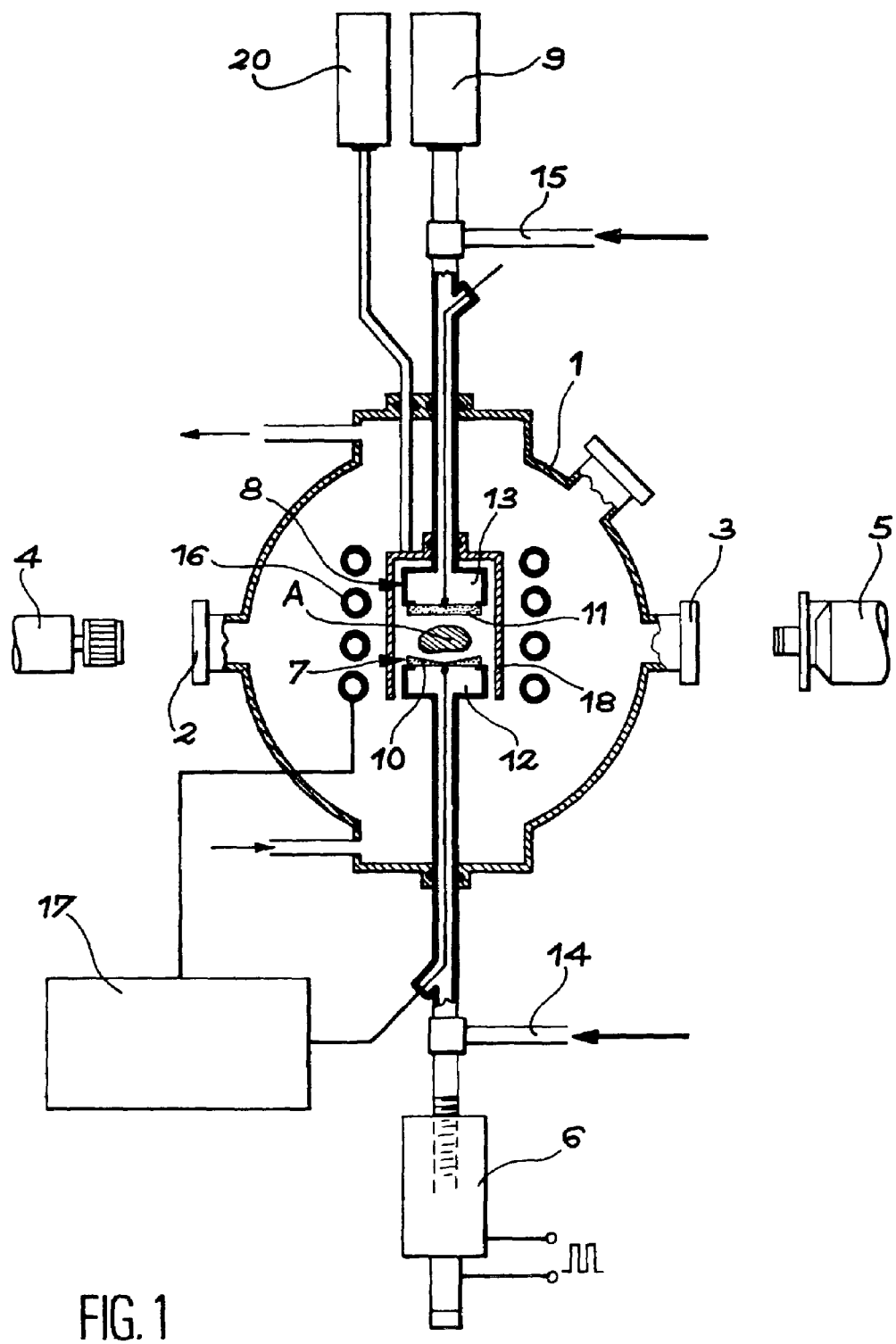

RELAXATION-TYPE VISCOSIMETER HAVING A MAGNETIC FIELD GENERATOR AND METHOD THEREFOR

The invention relates to a viscometer and a process for measuring the viscosity of a fluid and the shear rate sensitivity thereof.

There are a number of various viscometers and viscometry processes. Several of these rely on the displacement of a ball or a solid body in the fluid whose viscosity is to be measured; others measure the deformation rate of a fluid sample, in suspension or submitted to a constant load. The invention relates to the field of relaxation viscometry, where the fluid, split into drops by capillarity forces, is flattened for some time before being freed to recover its initial shape; the viscosity is derived from the rate of relaxation of the fluid.

This viscometry method features noticeable advantages: it is a fast measurement which involves a small amount of fluid, which proves very interesting for experimental products whose manufacturing is difficult or expensive; it applies to a wide range of viscosities; and finally, it implies no contact between the fluid and the viscometer parts, as this device is of "gas lifting type", which means that a gas flow is blown through a lower wedge-shaped plate, on which the drop is deposited, arid an upper plate intended far flattening the drop: the gas pressure maintains the fluid at a distance from the plates, so that neither chemical interaction occurs with the said plates, nor crystal germination when the fluid is diphasic. Preferably, the lower plate is wedge-shaped but it may have various other shapes.

The invention may apply to non-Newtonian fluids, whose viscosity coefficient varies according to the shearing rate of the fluid. The shear rate of a fluid $\gamma$ is defined as the gradient of the speed V along the direction z perpendicular to this speed, that is $\gamma=dV/dz$. The viscosity of Newtonian fluids may be directly derived by means of a correlation calculated over the time function following which the drop recovers its original shape, which is not possible with non-Newtonian fluid, as the shear rate of the drop decreases when the drop recovers its shape: the viscosity of such fluids varies during the trial.

The invention brings a solution to this problem, thanks to a viscometry process which applies to a drop of fluid which is flattened, then let free to recover its shape, with sequential measurements of the drop height along time, with the calculation of a characteristic relaxation time constant in terms of the measured heights, using a correlation function, then a viscosity calculation. The said calculations of the characteristic relaxation time constant and viscosity are carried out on various portions of measurement curves according to respective correlation functions, and a value of the shear rate of the drop is thus obtained for each of said measurement portions. In other words, the viscosity and apparent shear rate measurement process is characterized in that it comprises the steps of:

imposing a strain to the drop to modify the shape thereof:
relaxing the strain and measuring one of the geometrical dimensions of the fluid drop along time, the drop being submitted to a magnetic field then,
deriving the viscosity value of the fluid drop using the value of the characteristic relaxation time constant obtained from a correlation function.

The wording "geometrical dimensions" refers to various diameters of the drop. Preferably, the height of the drop is measured (diameter deformed along the axisymmetric axis).

It is advisable to perform several time the process while submitting the fluid to various magnetic field intensities. The proposed device, in the latter case, according to another aspect of the invention, becomes a viscometer including an upper plate and a lower plate facing each other which both may be moved along the vertical direction, the lower plate being for example wedge-shaped, characterized in that it includes a generator producing a magnetic field whose amplitude may be modulated in the space located between the said upper and lower plates. The generator may be an electromagnetic coil fitted with a removable screen located between the coil and the said space.

Figure 2:
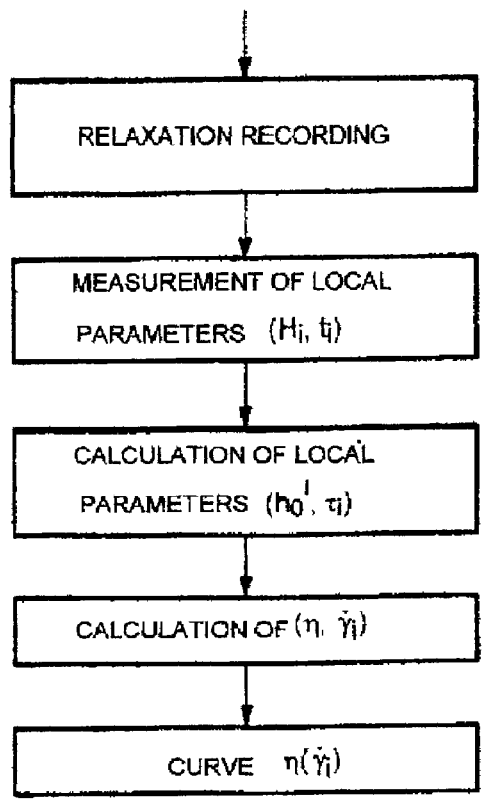
Figure 3:
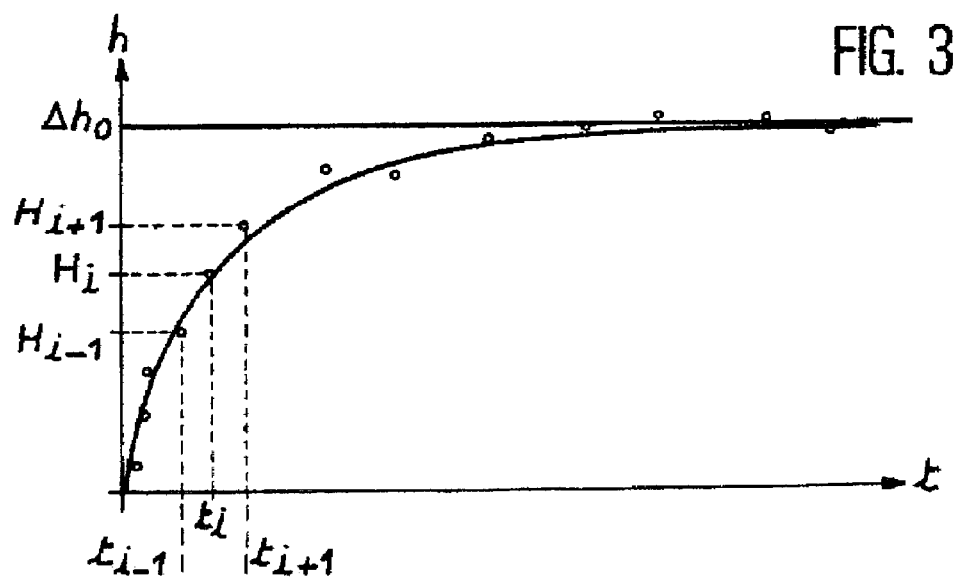

The invention will be described hereafter, with reference to the following figures, which show a preferred realization of the invention:

The FIG. 1 is an overall view of the viscometer according to the invention, the FIG. 2 is a diagram of the process and the FIG. 3 shows a measurement curve.

As seen on FIG. 1, the trial is performed in a heat-insulated enclosure fitted with windows 2, 3, intended for observing the trial evolution by means of a camera 4 and a pyrometer 5, in particular. The fluid sample A to be tested is deposited on a lower plate 7 whose upper face is concave and wedge-shaped; an upper plate 8 is vertically facing the lower plate. Moreover, a thrustor 9 and a lifter 6 fined with a step motor and an Archimedean screw move vertically the upper plate B and the lower plate 7 along the vertical direction, with a fast motion for the first one an a slow motion for the second one. According to the principle of contactless confinement, the gas is blown through the upper face 10 of the lower plate 7 and through the lower face 11 of the upper plate 8; these faces are porous and located in front of respective chambers 12 and 13 in which the gas is forced via ducts 14 and 15 entering the enclosure 1. When the pressure inside chambers 12 and 13 is high enough, the gas crosses the porous faces 10 and 11, creating in front of said faces a dynamic pressure large enough to make the sample A "float" in the gas, thus preventing any contact with said plates 8 and 9. The principle of confinement with gas lifting is described in the French patent 2 509 637, whereas the French patent 2 756 924 discloses a viscometer which operates according to this principle, the present invention being an improvement thereof. The prior viscometer corresponds to the previous description, and comprises also a heating device to warm the sample at the required temperature. The present viscometer distinguishes from the prior one in that, first, it must be provided with a generator producing a magnetic field in the volume surrounded by the coil 16, which includes the plates 7 and 8 as well as the sample A. Here, it is a coil 17 made of a conducting winding submitted to an AC potential difference with the plate 7 via a power supply 17, and which also warms the sample A by induction. Another magnetic generator, distinct from a warming means, could be used as well. Finally, a cylindrical magnetically shielding graphite screen separates the plates 7 and 8 from the coil 16, but it may be lifted via a thruster 20. The sample A is submitted to the magnetic field of the coil 16 or insulated from this field following the position (up or down) of the magnetically shielding screen 18, both situations being exploited to perform the measurement further described; thus the coil 16 is not a heating mean only.

The measurements to be carried out are detailed in the following. The lifting gas is blown through plates 7 and 8 and the sample A is introduced on the upper face 10 of the lower plate 7; if the sample A is a solid, it is heated till it reaches a pasty or fluid state and lifted over the upper face 10 of the lower plate 7; the capillarity forces make the sample to take a noticeably spherical form; the lower plate 7 is then slowly lifted till the drop reaches the upper plate 8, then lifted again by a quantity $\Delta h_0$, which induces a flattening of the drop. The upper plate 8 is then abruptly lifted up to free the sample A from strain.

The camera 4 records the evolution of the shape of sample A, which permits to measure the rate at which the drop recovers its initial shape, and, in particular, the height H(t) of its top at any time t. It is an oscillating phenomenon, which is aperiodic except for the fluids of very low viscosity, which may be characterised by a relaxation time constant .tau. which depends itself on the viscosity coefficient .eta. In the case of a Newtonian fluid, an aperiodic relaxation may be expressed by the relation (1);

$$h(t) = \Delta h_0 \cdot \left(1 - \exp\left(-\frac{t}{\tau}\right)\right)$$

where h=0 at the relaxing instant t=0 and h=$\Delta h_0$ when the drop has recovered its shape. A correlation calculation between the measured function h(t) and this exponential function yields the relaxation time constant τ; another way of doing, though less accurate, consists in applying a linear regression to the beginning of the measured curve. The relation (2):

$$\eta = \frac{40}{38} \frac{\sigma}{R} \times \tau$$

then gives the viscosity coefficient η in terms of the superficial tension σ of the material and the radius R of the drop.

These calculations are then valid for Newtonian fluids, in which case the relation σ=ρ×γ is pertinent; if the sample A proves to be non-Newtonian, i.e, if its viscosity ρ varies according to the shear rate γ, the relaxation of the drop induces a continuous variation of its viscosity ρ since the shear rate decreases as the drop recovers its initial shape one might think that these measurements are not suitable for such materials. It is not true, anyway, provided that a less simple process is involved, using local parameters of the relaxation curve: according to the invention, one calculates the slope of the relaxation curve following the relation (4):

$$\Delta_i = \frac{H_{i+1} - H_{i-1}}{t_{i+1} - t_{i-1}}$$

curve following the relation (4): where $H_{i-1}$, $H_i$ and $H_{i+1}$ are the heights of the top of the drop at times $t_{i-1}$, $t_i$ and $t_{i+1}$, assuming that the relaxation function may be locally expressed by the relation (5)

where the coefficient $\tau_i$ is the characteristic $$h_i(t) = h_0^i \cdot \left[1 - \exp\left(-\frac{t}{\tau_i}\right)\right]$$

relaxation time constant at this time. One uses the $$\tau_i = -\frac{H_i}{\Delta_i}$$

relations (6) and (7)

which yield the shear rate at this instant using the relation (8):

$$h_0^i = H_i \cdot \left[1 - \exp\left(-\frac{t_i}{H_i / \Delta_i}\right)\right]$$

$$(\gamma')_i = \frac{1}{l} \cdot \frac{h_0^i}{\tau_i}$$

where l is the characteristic shear length. The speed value V from relation (1) is here vertical, and the direction z is radial. As the drop stays symmetrically around the vertical axis, the shear is zero on the axis as well as at the equator and it is then adequate to retain for l half the value of the drop radius. The viscosity $\eta_i$ at this time is then evaluated using the $$Fg = \frac{Re}{lc} = \frac{\sqrt[3]{\frac{3}{4\pi} \frac{m}{\rho}}}{\frac{\sigma}{\rho g}}$$

relation (2). Corrections taking into account sphericity anomalies of the drop may be introduced. I particular, one may introduce the form factor Fg: where m is the sample mass, ρ its density, g the gravity constant, Re the equivalent radius and lc the capillary length; the relation (2) remains valid when Fg<1. One thus obtains the required data for plotting a curve which represents the viscosity η in terms of the shear rate γ'. The last step consists in estimating the sensitiveness of viscosity to the shear rate by means of a correlation over this curve, which amounts to calculate the coefficient n in the relation (9):

$$\eta = \eta_0 \times (\gamma')^{(n-1)}$$

The FIG. 2 sums up this process. It is though quite useful to get supplementary points of the curve η(γ') and the screen 18 is used for that purpose: the inventors had the idea of exploiting the magnetic field from coil 16 to produce a stirring inside the sample A, which modifies the shear rate γ' while keeping the contactless character of the trial. More precisely, one carries out one relaxation measurement with the magnetic field and one relaxation measurement without the field, once the screen 18 has been moved: actual trials have shown that the shear rates γ' belongs to truly separate regions, which improves the calculations for the coefficient η.

Any means for creating a magnetic field or stopping it or making it vary should be appropriate.

What is claimed is:

1. Viscometer including an upper plate (8) and a lower plate (7) facing each other and able to move along the vertical further comprising a generator (16, 18) of a magnetic field, and a means for modulating an amplitude of the magnetic field in a space between the upper elate and the lower plate, wherein the generator includes an electromagnetic coil (16) and the means for modulating includes a removable screen (18) located between said space and said coil, said screen being movable independently of the upper plate and of the lower plate.

2. Viscometer according to claim 1, wherein the coil surrounds the said space between the said plates and the screen is a vertically moving cylinder.

3. Viscometer for measuring a viscosity of a fluid sample and a shear rate sensitivity thereof including an upper plate (8) and a lower plate (7) facing each other and able to move along the vertical further comprising a generator (16, 18) of a magnetic field, and a means for modulating an amplitude of the magnetic field in a space containing the sample between the upper plate and the lower plate, wherein the generator includes an electromagnetic coil (16) surrounding the sample and the means for modulating includes a removable screen (18) located between said space and said coil, said screen being movable to and from a position in which it separates from the coil independently of the upper plate and of the lower plate.

4. Viscometer according to claim 3, wherein the coil surrounds the said space between the said plates and the screen is a vertically moving cylinder.

* * * * *

UNITED STATES PATENT AND TRADEMARK OFFICE
CERTIFICATE OF CORRECTION

PATENT NO. : 6,988,392 B2
DATED : January 24, 2006
INVENTOR(S) : Barbé et al.

It is certified that error appears in the above-identified patent and that said Letters Patent is hereby corrected as shown below:

Column 1,
Line 25, delete "arid" and insert -- and --.
Line 25, delete "far" and insert -- for --.

Column 2,
Line 23, delete "fined" and insert -- fitted --.
Line 25, delete "B" and insert -- 8 --.

Column 3,
Lines 39 and 41, delete "ρ" and insert -- η --.

Column 4,
Line 38, delete "Fg<1" and insert -- Fg≤1 --.
Line 66, delete "elate" and insert -- plate --.

Signed and Sealed this

Second Day of May, 2006

JON W. DUDAS
*Director of the United States Patent and Trademark Office*